(12) United States Patent
Chiamvimonvat et al.

(10) Patent No.: US 8,242,170 B2
(45) Date of Patent: Aug. 14, 2012

(54) USE OF CIS-EPOXYEICOSATRIENOIC ACIDS AND INHIBITORS OF SOLUBLE EPOXIDE HYDROLASE TO REDUCE CARDIOMYOPATHY

(75) Inventors: Nipavan Chiamvimonvat, Davis, CA (US); Bruce D. Hammock, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 853 days.

(21) Appl. No.: 11/921,676

(22) PCT Filed: Jun. 6, 2006

(86) PCT No.: PCT/US2006/022054
§ 371 (c)(1),
(2), (4) Date: Jan. 18, 2009

(87) PCT Pub. No.: WO2006/133257
PCT Pub. Date: Dec. 14, 2006

(65) Prior Publication Data
US 2009/0216318 A1 Aug. 27, 2009

Related U.S. Application Data

(60) Provisional application No. 60/688,172, filed on Jun. 6, 2005.

(51) Int. Cl.
*A01N 43/24* (2006.01)
*A61F 2/06* (2006.01)
*A61M 31/00* (2006.01)

(52) U.S. Cl. .................. 514/475; 623/1.42; 604/522

(58) Field of Classification Search .................. 514/475; 623/1.42; 604/522
See application file for complete search history.

(56) References Cited

U.S. PATENT DOCUMENTS

| | | | |
|---|---|---|---|
| 5,955,496 A | | 9/1999 | Hammock et al. |
| 6,531,506 B1 | | 3/2003 | Kroetz et al. |
| 6,831,082 B2 | | 12/2004 | Ingraham et al. |
| 2002/0077355 A1 | * | 6/2002 | Liao et al. ............... 514/475 |
| 2002/0165183 A1 | * | 11/2002 | Herweijer et al. ......... 514/44 |
| 2003/0023130 A1 | * | 1/2003 | Ciaccio et al. ........... 600/12 |
| 2003/0144198 A1 | * | 7/2003 | Collins ..................... 514/12 |
| 2004/0092567 A1 | | 5/2004 | Ingraham et al. |
| 2005/0222252 A1 | * | 10/2005 | Hammock et al. ....... 514/475 |

(Continued)

FOREIGN PATENT DOCUMENTS

WO WO 00/23060 4/2000

(Continued)

OTHER PUBLICATIONS

Lee et al. ("Effects of epoxyeicosatrienoic acids on the cardiac sodium channels in isolated rat ventricular myocytes," in Journal of Physiology (199), 519, 1, pp. 153-168).*

(Continued)

*Primary Examiner* — Blessing Fubara
(74) *Attorney, Agent, or Firm* — Weaver Austin Villeneuve and Sampson LLP

(57) ABSTRACT

The invention provides methods for inhibiting cardiomyopathy and for inhibiting cardiac arrhythmia, by administering to an individual in need thereof a cis-epoxyeicosantrienoic acid, an inhibitor of soluble epoxide hydrolase (sEH), or both. In some embodiments, the method comprises administering to the individual a nucleic acid encoding an inhibitor of sEH. Cardiomyopathies treatable by the methods of the invention include cardiac hypertrophy and dilated cardiomyopathy.

22 Claims, 6 Drawing Sheets

U.S. PATENT DOCUMENTS

2005/0288331 A1* 12/2005 Bush et al. .................. 514/325

FOREIGN PATENT DOCUMENTS

WO 2006/045119 4/2006

OTHER PUBLICATIONS

Lu et al. ("Stereospecific Activation of cardiac ATP-Sensitive K+ Channels by Epoxyeicosatrienoic Acids: A Structural Determinant Study" in American Society for Pharmacology and Experimental Therapeutics, Molecular Pharmacology, 62:1076-1083, 2002).*

Zhao et al. ("Soluble Epoxide Hydrolase Inhibition Protects the Kidney from Hypertension-Induced Damage" in Journal of American Society of Nephrology, vol. 15, pp. 1244-1253, 2004).*

Foley et al. ("Impact of hypertension on cardiomayopathy, morbidity and mortality in end-stage renal disease" in Kidney International, vol. 49, pp. 1379-1385, 1996).*

Lu et al "Stereospecific Actication of Cardiac ATP-Sensitive K+ Channels by Epoxyeicosatrienoic Acids: A Structured Determinant Study" in Molecular Pharmacology, 2002, vol. 62; pp. 1076-1083.

Karara et al. (Endogenous Epoxyeicosatrienoic Acids: Cytochrom P-450 Controlled Stereoselectivity of the Hepatic Arachidonic Acid Epoxygenase, The Journal of Biological Chemistry, Nov. 1989, vol. 264, No. 33, pp. 19822-19827.

Fang et al., "Pathways of Epoxyeicosatrienoic Acid Metabolism in Endothelial Cells: Implicatiin for the Vascular Effects of Soluble Epoxide Hydrolase Inhibitors," The Journal of Biological Chemistry, May 2001, vol. 276, No. 18, pp. 14867-14874.

Bedi "Inhaled Corticosteroids in COPD," Imdian J. Chest. Dis. Allied. Sci., 2005, vol. 47, pp. 243-244.

Morisseau et al., "Potent Urea and Carbanate Inhibitors of Soluble Epoxide Hydrolases," Proc. Natl. Acd. Sci. USA, Aug. 1999, vol. 96, pp. 8849-8854.

Sirna et al., "Cardia evaluation of the Patient with Stroke," Journal of the American Heart Association, 1990, vol. 21, pp. 14-23.

European Search Report mailed Jul. 16, 2009 for Application No. 06772386.6.

European First Office Action mailed Jan. 3, 2011 for Application No. 06772386.6.

International Search Report mailed Oct. 16, 2007 for PCT/US06/22054.

Lee et al. "Effects of epoxyeicosatrienic acids on the cardiac sodium channels in isolated rat ventricular myocytes", The Journal of Physiology, Aug. 15, 1999, vol. 519 Pt , pp. 153-168.

Xu, Danyan et al., "Prevention and reversal of cardiac hypertrophy by soluble epoxide hydrolase inhibitors", PNAS, Dec. 5, 2006, vol. 103, No. 49, pp. 18733-18738.

* cited by examiner

Control

Ag II alone

Ag II + 950

SEQUENCE LISTING

```
<160> NUMBER OF SEQ ID NOS: 38

<210> SEQ ID NO 1
<211> LENGTH: 554
<212> TYPE: PRT
<213> ORGANISM: Homo sapiens
<220> FEATURE:
<223> OTHER INFORMATION: Human soluble epoxide hydrolase (sEH)

<400> SEQUENCE: 1

Met Thr Leu Arg Gly Ala Val Phe Asp Leu Asp Gly Val Leu Ala Leu
1               5                   10                  15

Pro Ala Val Phe Gly Val Leu Gly Arg Thr Glu Glu Ala Leu Ala Leu
                20                  25                  30

Pro Arg Gly Leu Leu Asn Asp Ala Phe Gln Lys Gly Gly Pro Glu Gly
            35                  40                  45

Ala Thr Thr Arg Leu Met Lys Gly Glu Ile Thr Leu Ser Gln Trp Ile
        50                  55                  60

Pro Leu Met Glu Glu Asn Cys Arg Lys Cys Ser Glu Thr Ala Lys Val
65                  70                  75                  80

Cys Leu Pro Lys Asn Phe Ser Ile Lys Glu Ile Phe Asp Lys Ala Ile
                85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
    130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205

Ala Leu Lys Glu Leu Glu Lys Val Thr Gly Ile Gln Leu Leu Asn Thr
    210                 215                 220

Pro Ala Pro Leu Pro Thr Ser Cys Asn Pro Ser Asp Met Ser His Gly
```

```
                225                 230                 235                 240
Tyr Val Thr Val Lys Pro Arg Val Arg Leu His Phe Val Glu Leu Gly
                245                 250                 255

Trp Pro Ala Val Cys Leu Cys His Gly Phe Pro Glu Ser Trp Tyr Ser
            260                 265                 270

Trp Arg Tyr Gln Ile Pro Ala Leu Ala Gln Ala Gly Tyr Arg Val Leu
        275                 280                 285

Ala Met Asp Met Lys Gly Tyr Gly Glu Ser Ala Pro Pro Glu Ile
    290                 295                 300

Glu Glu Tyr Cys Met Glu Val Leu Cys Lys Glu Met Val Thr Phe Leu
305                 310                 315                 320

Asp Lys Leu Gly Leu Ser Gln Ala Val Phe Ile Gly His Asp Trp Gly
                325                 330                 335

Gly Met Leu Val Trp Tyr Met Ala Leu Phe Tyr Pro Glu Arg Val Arg
            340                 345                 350

Ala Val Ala Ser Leu Asn Thr Pro Phe Ile Pro Ala Asn Pro Asn Met
        355                 360                 365

Ser Pro Leu Glu Ser Ile Lys Ala Asn Pro Val Phe Asp Tyr Gln Leu
    370                 375                 380

Tyr Phe Gln Glu Pro Gly Val Ala Glu Ala Glu Leu Glu Gln Asn Leu
385                 390                 395                 400

Ser Arg Thr Phe Lys Ser Leu Phe Arg Ala Ser Asp Glu Ser Val Leu
                405                 410                 415

Ser Met His Lys Val Cys Glu Ala Gly Gly Leu Phe Val Asn Ser Pro
            420                 425                 430

Glu Glu Pro Ser Leu Ser Arg Met Val Thr Glu Glu Glu Ile Gln Phe
        435                 440                 445

Tyr Val Gln Gln Phe Lys Lys Ser Gly Phe Arg Gly Pro Leu Asn Trp
    450                 455                 460

Tyr Arg Asn Met Glu Arg Asn Trp Lys Trp Ala Cys Lys Ser Leu Gly
465                 470                 475                 480

Arg Lys Ile Leu Ile Pro Ala Leu Met Val Thr Ala Glu Lys Asp Phe
                485                 490                 495

Val Leu Val Pro Gln Met Ser Gln His Met Glu Asp Trp Ile Pro His
            500                 505                 510

Leu Lys Arg Gly His Ile Glu Asp Cys Gly His Trp Thr Gln Met Asp
        515                 520                 525

Lys Pro Thr Glu Val Asn Gln Ile Leu Ile Lys Trp Leu Asp Ser Asp
    530                 535                 540

Ala Arg Asn Pro Pro Val Val Ser Lys Met
545                 550

<210> SEQ ID NO 2
<211> LENGTH: 1665
<212> TYPE: DNA
<213> ORGANISM: Homo sapiens
<220> FEATURE:
<223> OTHER INFORMATION: Human soluble epoxide hydrolase (sEH)

<400> SEQUENCE: 2
atgacgctgc gcggcgccgt cttcgacctt gacggggtgc tggcgctgcc agcggtgttc      60
ggcgtcctcg gccgcacgga ggaggccctg cgctgcccca gggacttct gaatgatgct     120 ttccagaaag ggggaccaga gggtgccact acccggctta tgaaaggaga gatcacactt     180
tcccagtgga taccactcat ggaagaaaac tgcaggaagt gctccgagac cgctaaagtc     240
```

```
tgcctcccca agaatttctc cataaaagaa atctttgaca aggcgatttc agccagaaag    300
atcaaccgcc ccatgctcca ggcagctctc atgctcagga gaaaggatt cactactgcc    360 atcctcacca cacctggct ggacgaccgt gctgagagag atggcctggc ccagctgatg    420
tgtgagctga agatgcactt tgacttcctg atagagtcgt gtcaggtggg aatggtcaaa    480
cctgaacctc agatctacaa gtttctgctg acaccctga aggccagccc cagtgaggtc     540 gttttttgg atgacatcgg ggctaatctg aagccagccc gtgacttggg aatggtcacc     600
atcctggtcc aggacactga cacggccctg aaagaactgg agaaagtgac cggaatccag    660
cttctcaata ccccggcccc tctgccgacc tcttgcaatc caagtgacat gagccatggg    720
tacgtgacag taaagcccag ggtccgtctg cattttgtgg agctgggctg gcctgctgtg    780
tgcctctgcc atggatttcc cgagagttgg tattcttgga ggtaccagat ccctgctctg    840
gcccaggcag gttaccgggt cctagctatg gacatgaaag gctatggaga gtcatctgct    900
cctcccgaaa tagaagaata ttgcatggaa gtgttatgta aggagatggt aaccttcctg    960
gataaactgg gcctctctca agcagtgttc attggccatg actgggtgg catgctggtg    1020 tggtacatgg ctctcttcta ccccgagaga gtgagggcgg tggccagttt gaatactccc   1080
ttcataccag caaatcccaa catgtcccct ttggagagta tcaaagccaa cccagtattt   1140
gattaccagc tctacttcca agaaccagga gtggctgagg ctgaactgga acagaacctg   1200
agtcggactt tcaaaagcct cttcagagca agcgatgaga gtgttttatc catgcataaa   1260
gtctgtgaag cgggaggact ttttgtaaat agcccagaag agcccagcct cagcaggatg   1320
gtcactgagg aggaaatcca gttctatgtg cagcagttca agaagtctgg tttcagaggt   1380
cctctaaact ggtaccgaaa catggaaagg aactggaagt gggcttgcaa agcttgggga   1440
cggaagatcc tgattccggc cctgatggtc acggcggaga aggacttcgt gctcgttcct   1500
cagatgtccc agcacatgga ggactggatt cccacctga aaggggaca cattgaggac    1560 tgtgggcact ggacacagat ggacaagcca accgaggtga atcagatcct cattaagtgg    1620
ctggattctg atgcccggaa cccaccggtg gtctcaaaga tgtag                   1665
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic soluble epoxide hydrolase (sEH) target sequence

<400> SEQUENCE: 3
cagtgttcat tggccatgac tgg    23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic soluble epoxide hydrolase (sEH) sense-small interfering RNA (siRNA)
<220> FEATURE:
<223> OTHER INFORMATION: Description of Combined DNA/RNA Molecule: Synthetic soluble epoxide hydrolase (sEH) sense-small interfering RNA (siRNA)

<400> SEQUENCE: 4
guguucauug gccaugacut t    21

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) antisense-small
      interfering RNA (siRNA)
<220> FEATURE:
<223> OTHER INFORMATION: Description of Combined DNA/RNA Molecule:
      Synthetic soluble epoxide hydrolase (sEH) antisense-small
      interfering RNA (siRNA)

<400> SEQUENCE: 5
agucauggcc aaugaacact t                                           21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) target sequence

<400> SEQUENCE: 6
gaaaggctat ggagagtcat ctg                                         23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) sense-small
      interfering RNA (siRNA)
<220> FEATURE:
<223> OTHER INFORMATION: Description of Combined DNA/RNA Molecule:
      Synthetic soluble epoxide hydrolase (sEH) sense-small
      interfering RNA (siRNA)

<400> SEQUENCE: 7
aaggcuaugg agagucauct t                                           21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) antisense-small
      interfering RNA (siRNA)
<220> FEATURE:
<223> OTHER INFORMATION: Description of Combined DNA/RNA Molecule:
      Synthetic soluble epoxide hydrolase (sEH) antisense-small
      interfering RNA (siRNA)

<400> SEQUENCE: 8
gaugacucuc cauagccuut t                                           21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) target sequence

<400> SEQUENCE: 9
aaaggctatg gagagtcatc tgc                                         23
```

```
<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) sense-small interfering
      RNA (siRNA)
<220> FEATURE:
<223> OTHER INFORMATION: Description of Combined DNA/RNA Molecule:
      Synthetic soluble epoxide hydrolase (sEH) sense-small interfering
      RNA (siRNA)

<400> SEQUENCE: 10
aggcuaugga gagucaucut t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) antisense-small
      interfering RNA (siRNA)
<220> FEATURE:
<223> OTHER INFORMATION: Description of Combined DNA/RNA Molecule:
      Synthetic soluble epoxide hydrolase (sEH) antisense-small
      interfering RNA (siRNA)

<400> SEQUENCE: 11
agaugacucu ccauagccut t                                              21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) target sequence

<400> SEQUENCE: 12
caagcagtgt tcattggcca tga                                            23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) sense-small interfering
      RNA (siRNA)
<220> FEATURE:
<223> OTHER INFORMATION: Description of Combined DNA/RNA Molecule:
      Synthetic soluble epoxide hydrolase (sEH) sense-small interfering
      RNA (siRNA)

<400> SEQUENCE: 13
agcaguguuc auuggccaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) antisense-small
      interfering RNA (siRNA)
<220> FEATURE:
<223> OTHER INFORMATION: Description of Combined DNA/RNA Molecule:
      Synthetic soluble epoxide hydrolase (sEH) antisense-small
      interfering RNA (siRNA)
```

```
<400> SEQUENCE: 14
auggccaaug aacacugcut t                                               21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) target sequence

<400> SEQUENCE: 15
cagcacatgg aggactggat tcc                                             23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) sense-small interfering
      RNA (siRNA)
<220> FEATURE:
<223> OTHER INFORMATION: Description of Combined DNA/RNA Molecule:
      Synthetic soluble epoxide hydrolase (sEH) sense-small interfering
      RNA (siRNA)

<400> SEQUENCE: 16
gcacauggag gacuggauut t                                               21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) antisense-small
      interfering RNA (siRNA)
<220> FEATURE:
<223> OTHER INFORMATION: Description of Combined DNA/RNA Molecule:
      Synthetic soluble epoxide hydrolase (sEH) antisense-small
      interfering RNA (siRNA)

<400> SEQUENCE: 17
aauccagucc uccaugugct t                                               21

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      short spacer linking sense siRNA to reverse
      complementary antisense siRNA

<400> SEQUENCE: 18 ttcaagaga                                                              9

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) target sequence

<400> SEQUENCE: 19
cagtgttcat tggccatgac tgg                                             23
```

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) sense strand

<400> SEQUENCE: 20
gatccccgtg ttcattggcc atgactttca agagaagtca tggccaatga acactttttt      59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) antisense strand

<400> SEQUENCE: 21
agctaaaaag tgttcattgg ccatgacttc tcttgaaagt catggccaat gaacacggg       59

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) target sequence

<400> SEQUENCE: 22
gaaaggctat ggagagtcat ctg                                              23

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering  RNA (siRNA) sense strand

<400> SEQUENCE: 23
gatccccaag gctatggaga gtcatcttca agagagatga ctctccatag cctttttt        59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering  RNA (siRNA) antisense strand

<400> SEQUENCE: 24
agctaaaaaa aggctatgga gagtcatctc tcttgaagat gactctccat agccttggg       59

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering  RNA (siRNA) target sequence

<400> SEQUENCE: 25
aaaggctatg gagagtcatc tgc                                          23

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) sense strand

<400> SEQUENCE: 26
gatccccagg ctatggagag tcatctttca agagaagatg actctccata gccttttttt    59

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) antisense strand

<400> SEQUENCE: 27
agctaaaaaa ggctatggag agtcatcatc tcttgaaaga tgactctcca tagcctggg     59

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) target sequence

<400> SEQUENCE: 28
caagcagtgt tcattggcca tga                                          23

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) sense strand

<400> SEQUENCE: 29
gatccccagc agtgttcatt ggccatttca agagaatggc caatgaacac tgctttttt    59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) antisense strand

<400> SEQUENCE: 30
agctaaaaaa gcagtgttca ttggccattc tcttgaaatg gccaatgaac actgctggg    59

<210> SEQ ID NO 31
<211> LENGTH: 23
<212> TYPE: DNA
<213> ORGANISM: Artificial Sequence

```
<220> FEATURE:
<223> OTHER INFORMATION: Description of Artificial Sequence: Synthetic
      soluble epoxide hydrolase (sEH) short hairpin
      small interfering  RNA (siRNA) target sequence

<400> SEQUENCE: 31
cagcacatgg aggactggat tcc                                          23

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering  RNA (siRNA) sense strand

<400> SEQUENCE: 32
gatccccgca catggaggac tggattttca agagaaatcc agtcctccat gtgcttttt   59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering  RNA (siRNA) antisense strand

<400> SEQUENCE: 33
agctaaaaag cacatggagg actggatttc tcttgaaaat ccagtcctcc atgtgcggg   59

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 34
uguccagugc ccacaguccu                                              20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 35
uucccaccug acacgacucu                                              20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 36
guucagccuc agccacuccu                                              20

<210> SEQ ID NO 37
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 37
aguccucccg cuucacaga                                                  19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 38
gcccacuucc aguuccuuuc c                                               21
```

USE OF CIS-EPOXYEICOSATRIENOIC ACIDS AND INHIBITORS OF SOLUBLE EPOXIDE HYDROLASE TO REDUCE CARDIOMYOPATHY

CROSS-REFERENCES TO RELATED APPLICATIONS

This application is a 371 of PCT/US2006/022054 filed Jun. 6, 2006 and which claims benefit of benefit of U.S. Provisional Patent Application No. 60/688,172, filed Jun. 6, 2005, the contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 13, 2011 is named UCDVP021.txt and is 19,812 bytes in size.

BACKGROUND OF THE INVENTION

Cardiovascular disease is a leading cause of morbidity and mortality in the United States. (Levy et al., *N Engl J. Med.;* 322:1561-6 (1990); Ho et al., *J Am Coll Cardiol.;* 22:6A-13A (1993); Dominguez et al., *Cardiologia.;* 44:801-8 (1999)) Among cardiovascular diseases, cardiomyopathy, disease of the heart muscle, is one of the most common causes of heart failure and of requiring a heart transplant. Cardiomyopathy is generally divided into cardiac hypertrophy (or "hypertrophic cardiomyopathy"; the two terms are used synonymously herein), dilated cardiomyopathy, restrictive cardiomyopathy, and arrhythmogenic right ventricular cardiomyopathy (ARVC).

Sustained cardiac hypertrophy represents one of the most common causes leading to cardiac failure. (Frey et al., *Annu Rev Physiol.;* 65:45-79 (2003); Dorn and Molkentin, *Circulation.;* 109:150-8 (2004)) Once cardiac failure develops, the condition is associated with a very high mortality rate. Cardiac failure therefore represents an important and growing public health problem. Its increasing incidence and prevalence may be in part explained by the progressive aging of the world population. Estimates of prevalence of cardiac failure are 0.4 to 2% of the general population. Half of the patients carrying a diagnosis of heart failure will die within 4 years and patients with severe heart failure will die within 1 year.

In "dilated cardiomyopathy" (also known as "congestive cardiomyopathy"), the volume of the heart enlarges but the muscle becomes weaker. It is the most common form of cardiomyopathy, and often leads to congestive heart failure. Both dilated cardiomyopathy and cardiac hypertrophy are associated with an increased risk of cardiac arrhythmias and sudden cardiac death ("SCD").

At present, there are few effective pharmacologic therapies cardiac arrhythmias associated with cardiomyopathy and heart failure. Available antiarrhythmic drugs carry a high risk of proarrhythmias and other systemic side effects. (Ruskin, *N Engl J Med.;* 321:386-8 (1989)) A large number of patients who are deemed to be at high risk for SCD are now given implantable defibrillators, which are both costly and invasive. (Causes of death in the Antiarrhythmics Versus Implantable Defibrillators (AVID) *Trial. J Am Coll Cardiol.;* 34:1552-9 (1999); Moss, *Eur Heart J.;* 24:16-8 (2003); Moss, *J Cardiovasc Electrophysiol.;* 14:S96-8 (2003)).

It would be desirable to inhibit or reverse the development of cardiomyopathy and associated arrhythmias. The present invention fills these and other needs.

BRIEF SUMMARY OF THE INVENTION

The invention provides methods of inhibiting cardiomyopathy and of inhibiting cardiac arrhythmia. In a first group of embodiments, the methods comprise administering to a subject an effective amount of a cis-epoxyeicosantrienoic acid ("EET"), of an inhibitor of soluble epoxide hydrolase ("sEH"), or of a combination of an EET and an inhibitor of sEH, thereby inhibiting cardiomyopathy or inhibiting cardiac arrhythmia in the subject. In some embodiments, the cardiomyopathy inhibited is hypertrophic cardiomyopathy. In some embodiments, the cardiomyopathy inhibited is dilated cardiomyopathy. In some embodiments, the administration of the agent or agents inhibits cardiac arrhythmia. In some embodiments, the arrhythmia inhibited is atrial fibrillation. In some embodiments, the arrhythmia inhibited is ventricular fibrillation. In some embodiments, the arrhythmia inhibited is ventricular tachycardia. In some embodiments, the cardiac hypertrophy is due to valvular heart disease. In some embodiments, the valvular heart disease is secondary to rheumatic fever, myxomatous degeneration of the valve, or papillary muscle dysfunction. In some embodiments, the cardiac hypertrophy is due to a myocardial infarction. In some embodiments, the cardiac hypertrophy is due to familial hypertrophic cardiomyopathy. In some embodiments, the dilated cardiomyopathy is alcohol induced cardiomyopathy. In some embodiments, the dilated cardiomyopathy is familial dilated cardiomyopathy. In some embodiments, the dilated cardiomyopathy is caused by administration of an anti-cancer drug or exposure to a toxic agent. In some embodiments, the inhibitor of sEH is an adamantyl dodecyl urea. In some embodiments, the inhibitor of sEH is 12-(3-Adamantan-1-yl-ureido)dodecanoic acid, 12-(3-Adamantan-1-yl-ureido) dodecanoic acid butyl ester, Adamantan-1-yl-3-{5-[2-(2-ethoxyethoxy)ethoxy]pentyl}urea, or N-(1-acetylpiperidin-4-yl)-N'-(adamant-1-yl)urea. In some embodiments, the EET is selected from the group consisting of 14,15-EET, 8,9-EET and 11,12-EET. In some embodiments, the EET or the inhibitor of sEH, or both, are in a material which releases the EET, or inhibitor, or both, over time. The EET, or inhibitor of sEH, or both, can be released from a stent placed in a coronary artery. In some embodiments, the individual does not have hypertension, or is not being treated for hypertension with an inhibitor of sEH.

In another group of embodiments, the invention provides methods of inhibiting cardiomyopathy or cardiac arrhythmia in a subject by administering to the subject an isolated nucleic acid which inhibits expression of a gene encoding soluble epoxide hydrolase ("sEH"), thereby inhibiting cardiomyopathy or cardiac arrhythmia in the subject. In some embodiments, the method further comprises administering to the individual a cis-epoxyeicosantrienoic acid ("EET"). In some embodiments, the nucleic acid is a small interfering RNA ("siRNA"). In some embodiments, the cardiomyopathy is hypertrophic cardiomyopathy. In some embodiments, the cardiomyopathy is dilated cardiomyopathy. In some embodiments, the administration of said agent or agents inhibits cardiac arrhythmia. In some embodiments, the arrhythmia inhibited is atrial fibrillation. In some embodiments, the arrhythmia inhibited is ventricular fibrillation. In some embodiments, the arrhythmia inhibited is ventricular tachycardia. In some embodiments, the cardiac hypertrophy is due to valvular heart disease. In some embodiments, the valvular heart disease is secondary to rheumatic fever, myxomatous degeneration of the valve, or papillary muscle dysfunction. The nucleic acd can be released from a stent placed in a coronary artery. In some embodiments, the cardiac hypertrophy is due to a myocardial infarction. In some embodiments, the individual does not have hypertension, or is not being treated for hypertension with an inhibitor of sEH.

BRIEF DESCRIPTION OF THE DRAWINGS

FIGS. 2A and 2B. H&E-stained histologic sections of hearts of a sham-operated mouse (Control) and TAC-mice, showing cardiac hypertrophy at 3 weeks in the Control TAC-mouse. FIGS. 2C and 2D. Treatment of TAC-mice with compound 950 (15 mg/kg twice a day) or AUDA-BE (3 mg/kg twice a day) prevents the development of cardiac hypertrophy. All histologic sections are presented with the atria on top and the right ventricle to the left. Scale bar, 200 µm.

DETAILED DESCRIPTION OF THE INVENTION

Figure 1:
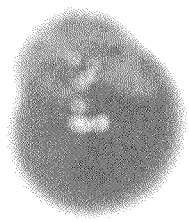
FIG. 1. Inhibition of cardiac hypertrophy in mice with thoracic aortic constriction ("TAC-mice") by sEH inhibitors. Examples of whole hearts from TAC-mice treated with compound 950 (hearts on left side and middle) compared to untreated TAC-mice (heart on right side). The mice were sacrificed after three weeks of follow up. Scale, 1 cm.

Introduction
A. EETs and sEHI for Prevention of Cardiomyopathy and Arrhythmias

Surprisingly, it has now been discovered that hypertrophic and dilated cardiomyopathy can be inhibited or even reversed, and atrial and ventricular arrhythmias can be inhibited, by the use of inhibitors of the enzyme known in the art as soluble epoxide hydrolase ("sEH"; inhibitors of this enzyme are sometimes referred to herein as "sEHI"). Moreover, it has now been discovered that the effects of sEH inhibitors can be increased by also administering cis-epoxyeicosantrienoic acids ("EETs"). The effect is at least additive over administering the two agents separately, and may indeed be synergistic. Even more surprisingly, it is believed that the inhibition or reversal of cardiomyopathy can be affected by administering EETs without also administering sEHIs.

In studies underlying the present invention, animals were subjected to thoracic aortic banding, a procedure in which the aorta is constricted. Aortic banding is a recognized model for inducing cardiac hypertrophy by increasing the pumping pressure required by the heart. Animals which underwent aortic banding and which were administered a sEHI did not develop cardiac hypertrophy, while control animals banded but not administered sEHI showed substantial enlargement of their hearts. Strikingly, animals which were first banded for three weeks, enlarging their hearts, and then administered a sEHI showed an almost complete resolution of cardiac hypertrophy, with their hearts returning to sizes which were normal or close to normal. The Examples section below reports the results of studies using two exemplar sEHI. The aortic banding studies reported in the Examples have also been repeated using a further exemplar sEHI, N-(1-acetylpiperidin-4-yl)-N'-(adamant-1-yl)urea, with similar results. The inhibition of cardiac hypertrophy by three different sEHI demonstrates that the effect is due to their shared biological activity in inhibiting the activity of sEH.

While cardiac hypertrophy results in part from the enlargement of individual cardiomyocytes, in clinical practice, it is usually confirmed clinically by measuring the thickness of the left ventricle. In the studies underlying the invention, these measurements were made following dissection of the hearts of animals used in the studies. In humans, measurement of the ventricle walls is typically made by echocardiography.

While the studies underlying the present invention involved a model for cardiac hypertrophy, it is believed that the results will also obtain for dilated cardiomyopathy. In dilated cardiomyopathy, as in cardiac hypertrophy, the heart enlarges, but instead of thickening, the heart muscle thins, becoming weak and less efficient at pumping. Typically, the body attempts to compensate for the decreased pumping power of the heart by increasing the amount of fluid, which in turn causes the heart to enlarge to accommodate the increased volume of blood flowing through it. The size of the heart, and the thickness of the muscle, can be determined by any of a number of standard methods, including echocardiography, by chest X-ray, and angiography.

Dilated cardiomyopathy is typically caused by heavy alcohol use, by exposure to drugs (including cancer chemotherapeutics, such as adriamycin), by exposure to other toxins, by genetic factors (in which case it is known more specifically as "familial cardiomyopathy"), and occasionally from pregnancy. Dilated cardiomyopathy can also be caused by a viral infection, typically by the Coxsackie B viruses (in which case it is often referred to more specifically as "viral myocarditis"). In a small subset of patients, it is caused by autoimmune disease. The practitioner usually determines the likely causation responsible for the dilated cardiomyopathy by the patient's history. In some preferred embodiments, the dilated cardiomyopathy is not due to viral infection or to autoimmune disease. In some embodiments, a patient who has viral myocarditis but who has not previously been treated with an sEHI or with an EET can be treated by the methods of the invention. It is not anticipated that the methods of the invention will benefit those persons with restrictive cardiomyopathy.

Surprisingly, sEHIs and, by extension, EETs, are also extremely effective in inhibiting or reducing cardiac arrhythmias. Thus, it is expected that persons who have arrhythmias due to (a) past myocardial infarctions, (b) valvular heart disease, (c) familial hypertrophic cardiomyopathy, (d) dilated cardiomyopathy or (e) a combination of two or more of these conditions, can have arrhythmias inhibited or eliminated by use of sEHIs, of EETs, or of both. This is important, since the sudden cardiac death caused by cardiac arrhythmia represents one of the most common causes of death in heart failure patients, occurring with roughly the same frequency as pump failure. In preferred embodiments, the persons with dilated cardiomyopathy have cardiomyopathy due to alcohol use, drug exposure, or familial cardiomyopathy, rather than to viral myocarditis or autoimmune disease. Again, it is not anticipated that the methods of the invention will benefit those persons with restrictive cardiomyopathy.

There are a variety of forms of arrhythmias. The effect of sEHIs on arrhythmias were studied on two of the most serious forms, atrial fibrillation and ventricular fibrillation, as an indicator of their effects on arrhythmias generally. According to the American College of Cardiology, some 3 to 5% of Americans have atrial fibrillation, which is most common in persons over 65. Ventricular arrhythmias are the most serious and life threatening. Ventricular fibrillation, in which the ventricles quiver ineffectively, can result in sudden cardiac death. The studies underlying the invention showed that sEHI, and by extension EETs, which are increased in the presence of sEHI, reduced both atrial fibrillation and ventricular fibrillation. Accordingly, both EETs and sEHI are expected to be useful for the treatment of arrhythmias generally and especially for the treatment or prevention of tachyarrhythmias, including atrial and ventricular fibrillation and ventricular tachycardia in persons who (a) have had a past myocardial infarction, (b) have valvular heart disease, (c) have familial hypertrophic cardiomyopathy, (d) have dilated cardiomyopathy or (e) have a combination of two or more of these conditions, provided that if dilated cardiomyopathy is present, it is due to alcohol use, drug exposure, or familial cardiomyopathy, rather than to viral myocarditis or autoimmune disease, and is not restrictive cardiomyopathy. It is also believed that the methods will be applicable to tachyarrhythmias due to arrhythmogenic right ventricular cardiomyopathy (ARVC).

Ventricular tachycardia can be considered to be a sequence of consecutive premature ventricular beats. Tachycardia lasting over 30 seconds is termed sustained ventricular tachycardia. Sustained ventricular tachycardia causes a drop in blood pressure, can lead to heart failure and, in its most serious form, leads to ventricular fibrillation and possible sudden cardiac death.

There are currently only a limited number of pharmacologic therapies for arrhythmias, such as amiodarone, a drug which can induce serious lung and liver disease. Thus, arrhythmias are usually treated by invasive means, such as surgery to cut the nerves that are misfiring or the implantation of electrical devices to control the heartbeat and to shock the out of fibrillation. These solutions are both invasive and expensive. Thus, the use of EETs and sEHI as therapeutics for arrhythmias is expected to provide a valuable, less invasive and less expensive alternative to surgical intervention.

As noted in the next section, it has previously been reported that sEH inhibitors can be used to treat hypertension. Other anti-hypertensive agents, however, are not known to reduce cardiac arrhythmia. Therefore, a person with hypertension whose hypertension is being adequately controlled by an anti-hypertensive agent other than an inhibitor of sEH who has or is at risk for arrhythmia (for example, a person who also had a heart attack or who has vavular heart disease) can still benefit from also taking a sEHI, an EET, or both an sEHI and an EET to inhibit the arrhythmia or to reduce the chance of developing one, so long as the use of the sEHI, EET, or combination of sEHI and EET does not cause the person's blood pressure to drop below normal levels.

Inhibitors of sEH stabilize not only EETs but also other epoxide-containing lipids in the body. For example, sEHI reduce the degradation of resolvins and leukotoxins. Thus, the beneficial effects seen in the studies underlying the present invention may be due in whole or in part to the stabilization of lipids other than EETs. Whatever the cause, however, the studies underlying the present invention indicate that sEHI have a powerful effect in reversing and reducing hypertrophic cardiomyopathy, dilated cardiomyopathy, and arrhythmias associated with these conditions. It is not contemplated that the methods of the invention will be applicable to restrictive cardiomyopathy.

Patients who can Benefit from Use of EETs or sEHI or Both

Hypertension is one cause of hypertrophic cardiomyopathy, and it has previously been reported that sEH inhibitors can be used to treat hypertension. See, U.S. Pat. Nos. 6,531, 506 and 6,693,130. Treatment of hypertension with anti-hypertensive agents is believed to reduce cardiac hypertrophy that is due to hypertension. See, e.g., Devereux et al., Circulation. 10(11):1456-62 (2004).

A number of conditions other than hypertension, however, also lead to cardiac hypertrophy, and treatment by anti-hypertension agents is not considered to reduce cardiac hypertrophy caused by conditions other than hypertension. These other conditions include, for example, (1) valvular heart disease, such as valvular heart disease secondary from rheumatic fever, myxomatous degeneration of the valve, papillary muscle dysfunction (for example, from myocardial infarction), or congenital deformities, (2) myocardial infarction, and (3) familial hypertrophic cardiomyopathy secondary to mutations of sarcomeric proteins or other proteins. Since anti-hypertensive agents do not affect the underlying cause of hypertrophy in individuals with these such conditions, it is not surprising that cardiac hypertrophy in these patients does not respond to anti-hypertension medications.

A myocardial infarction (more commonly known as a "heart attack"), for example, typically kills part of the heart. As explained in the Background section, above, the remaining cardiomyocytes typically enlarge, or hypertrophy, in an attempt to compensate for the pumping ability lost by the loss of the myocytes killed in the infarction. This enlargement then leads to cardiac failure. (Cardiac failure, also known as congestive heart failure, is a condition in which the heart loses the ability to pump efficiently, and is not to be confused with cardiac arrest, in which the heart ceases beating.) The enlargement of the cardiomyocytes, however, also tends to make them electrically unstable, and can itself be a cause of arrythmias, leading to sudden cardiac death. It is expected that the reduction in cardiac hypertrophy resulting from the use of EETs, sEHI, or of a combination of the two, will inhibit arrythmias and will in turn reduce the incidence of sudden cardiac death from heart failure associated with cardiac hypertrophy.

Although an infarction can be caused in whole or in part by atherosclerosis, that is not the only cause of an infarction. Thus, persons who have undergone an infarction may or may not have atherosclerosis. Further, the cardiomyocytes which undergo hypertrophy are not endothelial cells, such as those lining the blood vessels. Thus, there is no reason to expect that agents which might affect endothelial cell function would have any effect on reducing hypertrophy of cardiomyocytes.

As noted above, hypertension is one cause of cardiac hypertrophy, and it has previously been taught that hypertension can be treated with sEHI. Hypertension can, of course, also be treated with agents other than EETs and sEHI. The present invention, however, shows that treatment of hypertension with sEHI, EETs, or both, however, will also have the benefit of reducing cardiac hypertrophy and cardiac arrhythmias in the patient, and is therefore to be preferred over the use of other anti-hypertensive agents. Patients with or without hypertension who have episodes of non-sustained ventricular tachycardia will especially benefit from the methods of the invention since the compositions used in the methods should be safer than currently available anti-arrhythmia drugs.

In some embodiments of the invention, the person being treated with EETs, sEHI, or both, does not have hypertension or is not currently being treated with an anti-hypertension agent that is an inhibitor of sEH. In some embodiments, the person being treated does not have inflammation or, if he or she has inflammation, has not been treated with an sEH inhibitor as an anti-inflammatory agent. In some preferred embodiments, the person is being treated for inflammation by an anti-inflammatory agent, such as a steroid, that is not an inhibitor of sEH. Whether or not any particular anti-inflammatory or anti-hypertensive agent is also an sEH inhibitor can be readily determined by standard assays, such as those taught in U.S. Pat. No. 5,955,496.

In some embodiments, the patient's disease or condition is not caused by an autoimmune disease or a disorder associated with a T-lymphocyte mediated immune function autoimmune response. In some embodiments, the patient does not have a pathological condition selected from type 1 or type 2 diabetes, insulin resistance syndrome, atherosclerosis, coronary artery disease, angina, ischemia, ischemic stroke, Raynaud's disease, or renal disease. In some embodiments, the patient is not a person with diabetes mellitus whose blood pressure is 130/80 or less, a person with metabolic syndrome whose blood pressure is less than 130/85, a person with a triglyceride level over 215 mg/dL, or a person with a cholesterol level over 200 mg/dL or is a person with one or more of these conditions who is not taking an inhibitor of sEH. In some embodiments, the patient does not have an obstructive pulmonary disease, an interstitial lung disease, or asthma. In some embodiments, the patient is not also currently being treated with an inhibitor of one or more enzymes selected from the group consisting of cyclo-oxygenase ("COX")-1, COX-2, and 5-lipoxygenase ("5-LOX"), or 5-lipoxygenase activating protein ("FLAP"). It is noted that many people take a daily low dose of aspirin (e.g., 81 mg) to reduce their chance of heart attack, or take an occasional aspirin to relieve a head ache. It is not contemplated that persons taking low dose aspirin to reduce the risk of heart attack would ordinarily take that aspirin in combination with an EET or sEHI to potentiate that effect. It is also not contemplated that persons taking an occasional aspirin or ibuprofen tablet to relieve a headache or other episodic minor aches or pain would ordinarily take that tablet in combination with an EET or sEHI to potentiate that pain relief, as opposed to persons seeking relief for chronic pain from arthritis or other conditions requiring significant pain relief over an extended period. In some embodiments, therefore, the patient being treated by the methods of the invention may have taken an inhibitor of COX-1, COX-2, or 5-LOX in low doses, or taken such an inhibitor on an occasional basis to relieve an occasional minor ache or pain. In some embodiments, the patient with dilated cardiomyopathy has dilated cardiomyopathy that is drug induced, due to alcoholism, or due to familial cardiomyopathy, rather than dilated cardiomyopathy due to viral infection or autoimmune disease.

Medicaments of EETs can be made which can be administered by themselves or in conjunction with one or more sEH inhibitors, or a medicament containing one or more sEH inhibitors can optionally contain one or more EETs. The EETs can be administered alone, or concurrently with a sEH inhibitor or following administration of a sEH inhibitor. It is understood that, like all drugs, sEH inhibitors have half lives defined by the rate at which they are metabolized by or excreted from the body, and that the sEH inhibitor will have a period following administration during which it will be present in amounts sufficient to be effective. If EETs administered after an sEH inhibitor are intended to be administered while the sEH inhibition is still in effect, therefore, it is desirable that the EETs be administered during the period during which the inhibitor will be present in amounts to be effective to delay hydrolysis of the EETs. Typically, in such a situation, the EET or EETs will be administered within 48 hours of administering an sEH inhibitor. More preferably, where the effect of the EET or EETs is intended to be enhanced by the effect of an sEHI, the EET or EETs are administered within 24 hours of the inhibitor, and even more preferably within 12 hours. In increasing order of desirability, the EET or EETs are administered within 10, 8, 6, 4, 2, hours, 1 hour, or one half hour after administration of the inhibitor. Most preferably, the EET or EETs are administered concurrently with the inhibitor. In some embodiments, the person being treated with the EET or EETs does not have one of the disorders listed above as a condition which the subject being treated with an sEHI does not have. In some embodiments, the person being treated with the EET or EETs is not being treated for atherosclerosis, other inflammatory conditions, or other conditions in which inhibition of adhesion molecule expression, particularly on endothelial cells, is desirable.

In some embodiments, the sEH inhibitor may be a nucleic acid, such as a small interfering RNA (siRNA) or a micro RNA (miRNA), which reduces expression of a gene encoding sEH. Optionally, EETs may be administered in combination with such a nucleic acid. Typically, a study will determine the time following administration of the nucleic acid before a decrease is seen in levels of sEH. The EET or EETs are typically then administered at a time calculated to be after expression of the nucleic acid has resulted in a decrease in sEH levels.

In some embodiments, the EETs, the sEH inhibitor, or both, are provided in a material that permits them to be released over time to provide a longer duration of action. Slow release coatings are well known in the pharmaceutical art; the choice of the particular slow release coating is not critical to the practice of the present invention.

In some embodiments, it may not be desirable that the person being treated for cardiac hypertrophy or dilated cardiomyopathy be contacted with sEHIs systemically. In such instances, it may be desirable to administer the sEHI as a "soft drug." A soft drug is an analog (often isosteric or isoelectronic, or both) of a compound designed to be metabolized into an inactive form after it exerts the desired effect. Typically, the drug is administered locally, where it exerts the desired effect, and is metabolized into an inactive form as it distributes away from the intended site of action. For example, soft drug forms of sEHI are esters that can be degraded by endogenous esterases. Typically, for sEHI that have carbonyl groups, the ester is created near the carbonyl. The soft drug form of the sEHI may be embedded in a material to be released over time, and the material implanted near the heart to provide the drug locally to the heart. For example, the soft drug form of sEHI can be embedded in the coating of a stent or otherwise placed on the stent in a releasable form, and the stent then placed in a coronary artery to bathe the heart tissue supplied by the artery with the soft drug sEHI. Alternatively, in embodiments in which systemic sEHI exposure is not a concern, ordinary sEHIs (that is, sEHIs that are not in a soft drug form, and optionally with one or more EETs) can be embedded in the stent coating or otherwise placed on the stent in a releasable form to provide locally high levels of sEHI and EETs to the heart tissue supplied by the artery. Similarly, a nucleic acid which inhibits expression of sEH can be embedded in the stent or otherwise placed on the stent in a releasable form, to provide the nucleic acid to the heart tissue upon release of the nucleic acid from the stent.

Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 epoxygenases. As discussed further in a separate section below, while the use of unmodified EETs is the most preferred, derivatives of EETs, such as amides and esters (both natural and synthetic), EETs analogs, and EETs optical isomers can all be used in the methods of the invention, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH") is an epoxide hydrolase which in endothelial and smooth muscle cells converts EETs to dihydroxy derivatives called dihydroxyeicosatrienoic acids ("DHETs"). The cloning and sequence of the murine sEH is set forth in Grant et al., J. Biol. Chem. 268(23): 17628-17633 (1993). The cloning, sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

"Valvular heart disease" refers to a disorder of any one of the four valves of the heart. More particularly in the context of the present invention, it refers to conditions in which the disorder increases pressure in a chamber or chambers of the heart. For example, mitral valve insufficiency permits some blood to flow back from the left ventricle into the left atrium rather than into the aorta, increasing the pressure in the atrium.

"Fibrillation," as defined on the website of the American College of Cardiology, is an abnormal, uncontrolled rapid contraction of the fibers in the heart. It further states: "When the process involves the two upper chambers of the heart (the atria), the condition is called 'atrial fibrillation.' When it involves the lower, ventricular chambers, the condition is called 'ventricular fibrillation.'"

An "arrhythmia" is a disorder of the regular rhythmic beating of the heart. As used herein, the term refers to atrial or ventricular fibrillation.

"Arrhythmogenic right ventricular cardiomyopathy" or "ARVC" is a recently recognized form of cardiomyopathy in which electrical disturbances affect the functioning of the right ventricle more than the left ventricle. According to the website of the Cardiomyopathy Association, it is defined as a heart muscle disease characterized by the replacement of heart muscle by fibrous scar and fatty tissue, and has acquired several names, all of which denote the same condition. In addition to ARVC, the most common term, it has also been called Arrhythmogenic Right Ventricular Dysplasia/Cardiomyopathy (ARVD/C) and Arrhythmogenic Right Ventricular Dysplasia (ARVD). It is thought to affect between 1:3,000 and 1:10,000 people.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm *C. elegans* in the early 1990s and are now known in many species, including humans. As used herein, it refers to exogenously administered miRNA unless specifically noted or otherwise required by context.

With respect to cardiac arrhythmias, "inhibiting" means that the recurrence of such arrhythmias are reduced or eliminated, or that the duration of such arrhythmias is reduced, or both. With respect to cardiac hypertrophy or dilated cardiomyopathy, "inhibiting" means (i) the prevention of the development of the condition in a subject at risk thereof or (ii) in the case of a subject with cardiac hypertrophy, the reversal of hypertrophy.

Cardiac Hypertrophy

Cardiomyocytes are terminally differentiated cells. In response to various extracellular stimuli, cardiomyocytes grow in a hypertrophic manner, an event that is characterized by enlargement of individual cell size, an increase in the content of contractile proteins such as myosin heavy chain, and expression of embryonic genes such as atrial natriuretic factor (ANF). (Chien et al., Faseb J.; 5:3037-46 (1991); Chien, Cardiologia.; 37:95-103 (1992); Chien, J Clin Invest.; 105:1339-42 (2000)) The collective result is cardiac hypertrophy, which is an adaptive and compensatory response in nature. The initial or compensated stage of hypertrophy normalizes wall stress per unit of myocardium and is thus a basic mechanism for maintaining normal chamber function. (Grossman et al, J Clin Invest.; 56:56-64 (1975)) However, this process is a double-edged sword: sustained cardiac hypertrophy will eventually lead to overt heart failure.

In most instances, heart failure is the final consequence of many underlying disease etiologies such as long-standing hypertension, coronary heart disease, valvular insufficiency, arrhythmia, viral myocarditis, and mutations in sarcomere-encoding genes. A compensatory enlargement of the myocardium, or hypertrophy, typically accompanies many of these predisposing insults and is a leading predictor for the development of more serious and life-threatening disease. Decompensated hypertrophy occurs if increased cardiac mass fails to normalize wall stress and the contractile function is not sufficient to maintain normal pump function. This is associated with clinical and pathological features of congestion.

Cardiac hypertrophy is characterized by an increase in heart-to-body weight ratio and an increase in the size of the individual cardiac myocytes, enhanced protein synthesis, and heightened organization of the sarcomere. Classically, two different hypertrophic phenotypes can be distinguished: (1) concentric hypertrophy due to pressure overload, which is characterized by parallel addition of sarcomeres and lateral growth of individual cardiomyocytes, and (2) eccentric hypertrophy due to volume overload or prior infarction, characterized by addition of sarcomeres in series and longitudinal cell growth. (Dorn et al., Circ Res.; 92:1171-5 (2003)). At the molecular level, these changes in cellular phenotype are accompanied by reinduction of the so-called fetal gene program, because patterns of gene expression mimic those seen during embryonic development. (Chien et al., Faseb J; 5:3037-46 (1991); Chien K R, Cardiologia.; 37:95-103 (1992)).

Hypertrophic transformation of the heart can be divided into three stages: (1) developing hypertrophy, in which load exceeds output, (2) compensatory hypertrophy, in which the workload/mass ratio is normalized and resting cardiac output is maintained, and (3) overt heart failure, with ventricular dilation and progressive declines in cardiac output despite continuous activation of the hypertrophic program. (Meerson F Z, Cor Vasa.; 3:161-77 (1961)). The late-phase "remodeling" process that leads to failure is associated with functional perturbations of cellular $Ca^{2+}$ homeostasis (Bers D M, Nature.; 415:198-205 (2002); Bers D M, Circ Res.; 90:14-7 (2002)) and ionic currents, (Ahmmed et al., Circ Res.; 86(5): 558-70 (2000); Kääb et al., Circ Res.; 78:262-273 (1996); Kääb et al., Circulation.; 98:1383-93 (1998)) which contribute to an adverse prognosis by predisposing to ventricular dysfunction and malignant arrhythmia. Significant morphological changes include increased rates of apoptosis, (Haunstetter A and Izumo S, Circ Res.; 86:371-6 (2000)) fibrosis, and chamber dilation.

The dichotomy between adaptive and maladaptive hypertrophy has been appreciated for some time, and the mechanisms that determine how long-standing hypertrophy ultimately progresses to overt heart failure are in the process of being elucidated. One biochemical hallmark of left ventricular hypertrophy induced by pressure overload is a shift in myosin isoform from α- to β-myosin heavy chains. (Delcayre C and Swynghedauw B, Pflügers Arch.; 355:39-47 (1975)). This alteration in myosin isoform expression result from transcriptionally mediated alteration in gene expression. (Boehler et al., J Biol. Chem.; 267:12979-12985 (1992)). Various lines of evidence suggest a decrease in the expression of the sarcoplasmic reticulum $Ca^{2+}$-cycling protein, $Ca^{2+}$ ATPase during the development of heart failure in several animal models, including humans with end-stage congestive heart failure, even though no changes can be detected during the compensated hypertrophied stage. (Kiss et al., Circ Res.; 77:759-764 (1995); Feldman et al., Circulation.; 75:331-9 (1987); Arai et al, Circ Res.; 72:463-469 (1993)). These changes are associated with a decrease in sarcoplasmic reticulum $Ca^{2+}$ transport. In addition, there are alterations in the level of phospholamban, sarcoplasmic reticulum $Ca^{2+}$-release channels and in $Ca^{2+}$ cycling proteins in the myofibrils and sarcolemma in different animal models with heart failure. (de la Bastie et al., Circ Res.; 66:554-564 (1990); Mercadier et al., J Clin Invest.; 85:305-309 (1990)). These studies suggest that critical components of the $Ca^{2+}$ cycling system may be responsible, in part, for the transitions between compensated pressure-overload hypertrophy and congestive heart failure.

Hypertrophy that occurs as a consequence of pressure overload is termed "compensatory" on the premise that it facilitates ejection performance by normalizing systolic wall stress. Recent experimental results, however, call into question the necessity of normalization of wall stress that results from hypertrophic growth of the heart. These findings, largely from studies in genetically engineered mice, raise the prospect of modulating hypertrophic growth of the myocardium to afford clinical benefit without provoking hemodynamic compromise. (Frey et al., supra, Dorn and Molkentin, supra; Frey et al., Circulation.; 109:1580-9 (2004)).

It is generally accepted that cardiac hypertrophy can be adaptive in some situations, for example, in athletes. However, it is less clear if a hypertrophic response to pathological situations, such as valvular heart disease, chronic arterial hypertension or a myocardial infarction, is initially a compensatory response and later becomes maladaptive or if this type of myocardial growth is detrimental from the outset.

It has been demonstrated that these different types of cardiac hypertrophy differ both at the morphological as well as the molecular level. Exercise-induced cardiac hypertrophy is generally not accompanied by an accumulation of collagen in the myocardium and usually does not exceed a modest increase in ventricular wall thickness. In addition, there are significantly differences in the expression levels for several hypertrophic genes, such as BNP or ET-1. Further, the isoform expression of α-/β-MHCs is regulated in opposite directions in exercise versus pressure overload-induced cardiac hypertrophy. However, some hypertrophic pathways, such as calcineurin-dependent signaling, appear to be activated in both pathological and physiological exercise-induced hypertrophy, as demonstrated by the finding that the calcineurin inhibitor can attenuate both phenotypes. Taken together, these data indicate that exercise-associated (physiologic) versus pathologic hypertrophy differ at the molecular level, but this does not exclude the possibility that certain pathways may be involved in all phenotypes of cardiac hypertrophy.

Since adult cardiomyocytes are terminally differentiated cells, many of the same intracellular signaling pathways that regulate proliferation in cancer cells or immune cells instead regulate hypertrophic growth of cardiomyocytes. The hypertrophic growth can be initiated by endocrine, paracrine, and autocrine factors that stimulate a wide array of membrane-bound receptors. Their activation results in the triggering of multiple cytoplasmic signal transduction cascades, which ultimately affects nuclear factors and the regulation of gene expression. It has previously been documented that no single intracellular transduction cascade regulates cardiomyocyte hypertrophy in isolation, but instead each pathway operates as an integrated component between interdependent and cross-talking networks. Therefore, blockade of specific intracellular signaling pathways in the heart can dramatically affect the entire hypertrophic response and effectively decrease cardiac hypertrophy. Furthermore, specific activation of a number of discrete signal transduction pathways may be sufficient to activate the entire hypertrophic response through effects on other cross-talking signaling networks.

Valvular Heart Disease

The heart has four valves: the mitral valve (the only valve with two flaps), the tricuspid, with three differently sized flaps, the aortic valve, which opens to allow blood from the heart into the aorta, and the pulmonary valve. A number of disorders affecting the valves can result in increased pressure in the chambers of the heart, which in turn can result in cardiac hypertrophy. These conditions include mitral valve stenosis, mitral valve insufficiency, aortic valve insufficiency, aortic valve stenosis, and tricuspid valve insufficiency. Several of these conditions occur in persons who had undiagnosed or incompletely treated rheumatic fever as a child. Rheumatic fever occurs most often in children who have a streptococcal throat infection ("strep throat"), and can result in mitral stenosis, tricuspid stenosis, aortic insufficiency, aortic stenosis, multivalvular involvement or, less commonly, pulmonic stenosis. Unlike stenosis of blood vessels, which is typically caused by a build up of lipids and cells on the interior of the vessel lumen, stenosis of heart valves is typically due to fusing of the flaps, to a build up of calcium on the flap, causing it to harden, to a congenital deformity, a weakening of valve tissue ("myxomatous degeneration"), or use of certain medicines, such as fenfluramine and dexfenfluramine.

Inhibitors of Soluble Epoxide Hydrolase

Scores of sEH inhibitors are known, of a variety of chemical structures. Derivatives in which the urea, carbamate, or amide pharmacophore (as used herein, "pharmacophore" refers to the section of the structure of a ligand that binds to the sEH) is covalently bound to both an adamantane and to a 12 carbon chain dodecane are particularly useful as sEH inhibitors. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999), which provides substantial guidance on designing urea derivatives that inhibit the enzyme.

Derivatives of urea are transition state mimetics that form a preferred group of sEH inhibitors. Within this group, N,N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-admamantyl ureas have been tested and have about the same high activity as an inhibitor of sEH.) Thus, isomers of adamantyl dodecyl urea are preferred inhibitors. It is further expected that N,N'-dodecyl-cyclohexyl urea (DCU), and other inhibitors of sEH, and particularly dodecanoic acid ester derivatives of urea, are suitable for use in the methods of the invention. Preferred inhibitors include:

12-(3-Adamantan-1-yl-ureido)dodecanoic acid (AUDA),

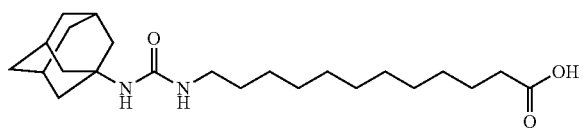

12-(3-Adamantan-1-yl-ureido)dodecanoic acid butyl ester (AUDA-BE),

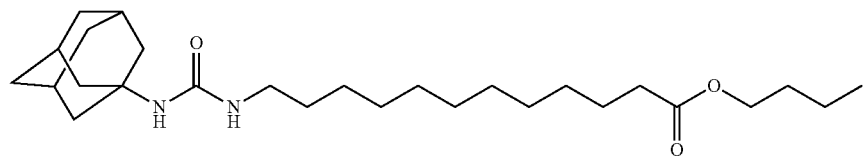

Adamantan-1-yl-3-{5-[2-(2-ethoxyethoxy)ethoxy]pentyl}urea (compound 950), and

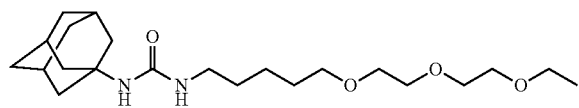

N-(1-acetylpiperidin-4-yl)-N'-(adamant-1-yl)urea (compound 1153).

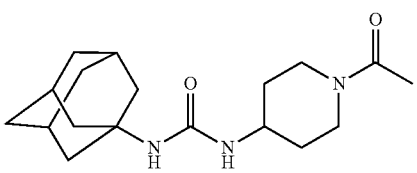

A number of other inhibitors which can be used in the methods and compositions of the invention are set forth in co-owned applications PCT/US2004/010298 and U.S. Published Patent Application Publication 2005/0026844.

U.S. Pat. No. 5,955,496 (the '496 patent) also sets forth a number of epoxide hydrolase inhibitors which can be use in the methods of the invention. One category of these inhibitors comprises inhibitors that mimic the substrate for the enzyme.

The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods of the invention are set forth in U.S. Pat. Nos. 6,150,415 (the '415 patent) and 6,531,506 (the '506 patent). Two preferred classes of inhibitors of the invention are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty inhibitors of Formula 2, which were shown to inhibit human sEH at concentrations as low as 0.1 µM. Any particular inhibitor can readily be tested to determine whether it will work in the methods of the invention by standard assays, such as that set forth in the Examples, below. Esters and salts of the various compounds discussed above or in the cited patents, for example, can be readily tested by these assays for their use in the methods of the invention.

As noted above, chalcone oxides can serve as an alternate substrate for the enzyme. While chalcone oxides have half lives which depend in part on the particular structure, as a group the chalcone oxides tend to have relatively short half lives (a drug's half life is usually defined as the time for the concentration of the drug to drop to half its original value. See, e.g., Thomas, G., Medicinal Chemistry: an introduction, John Wiley & Sons Ltd. (West Sussex, England, 2000)). Since the uses of the invention contemplate inhibition of sEH over periods of time which can be measured in days, weeks, or months, chalcone oxides, and other inhibitors which have a half life whose duration is shorter than the practitioner deems desirable, are preferably administered in a manner which provides the agent over a period of time. For example, the inhibitor can be provided in materials that release the inhibitor slowly, including materials that release the inhibitor in or near the kidney, to provide a high local concentration. Methods of administration that permit high local concentrations of an inhibitor over a period of time are known, and are not limited to use with inhibitors which have short half lives although, for inhibitors with a relatively short half life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an α/β-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors of the invention mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

Preferably, the inhibitor inhibits sEH without also significantly inhibiting microsomal epoxide hydrolase ("mEH"). Preferably, at concentrations of 500 µM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 500 µM. Inhibitors with $IC_{50}$s of less than 500 µM are preferred, with $IC_{50}$s of less than 100 µM being more preferred and, in order of increasing preference, an IC50 of 50 µM, 40 µM, 30 µM, 25 µM, 20 µM, 15 µM, 10 µM, 5 µM, 3 µM, 2 µM, 1 µM or even less being still more preferred. Assays for determining sEH activity are known in the art and described elsewhere herein.

EETs

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has long been believed that EETs administered systemically would be hydrolyzed too quickly by endogenous sEH to be helpful. In the only prior report of EETs administration of which we are aware, EETs were administered by catheters inserted into mouse aortas. The EETs were infused continuously during the course of the experiment because of concerns over the short half life of the EETs. See, Liao and Zeldin, International Publication WO 01/10438 (hereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

In studies from the laboratory of one of the present inventors, however, it has been shown that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of one of the present inventors have now shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus, EETs can be administered without also administering an sEHI to provide a therapeutic effect. Moreover, we have found that EETs, if not exposed to acidic conditions or to sEH are stable and can withstand reasonable storage, handling and administration.

In short, sEHI, EETs, or co-administration of sEHIs and of EETs, can be used to inhibit the development of, or reverse the presence of, cardiac hypertrophy, of dilated cardiomyopathy, and of atrial and of ventricular fibrillation. In some embodiments, one or more EETs are administered to the patient without also administering an sEHI. In some embodiments, one or more EETs are administered shortly before or concurrently with administration of an sEH inhibitor to slow hydrolysis of the EET or EETs. In some embodiments, one or more EETs are administered after administration of an sEH inhibitor, but before the level of the sEHI has diminished below a level effective to slow the hydrolysis of the EETs.

EETs useful in the methods of the present invention include 14,15-EET, 8,9-EET and 11,12-EET, and 5,6 EETs. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

If desired, EETs, analogs, or derivatives that retain activity can be used in place of or in combination with unmodified EETs. Liao and Zeldin, supra, define EET analogs as compounds with structural substitutions or alterations in an EET, and include structural analogs in which one or more EET olefins are removed or replaced with acetylene or cyclopropane groups, analogs in which the epoxide moiety is replaced with oxitane or furan rings and heteroatom analogs. In other analogs, the epoxide moiety is replaced with ether, alkoxides, difluorocycloprane, or carbonyl, while in others, the carboxylic acid moiety is replaced with a commonly used mimic, such as a nitrogen heterocycle, a sulfonamide, or another polar functionality. In preferred forms, the analogs or derivatives are relatively stable as compared to an unmodified EET because they are more resistant than an EET to sEH and to chemical breakdown. "Relatively stable" means the rate of hydrolysis by sEH is at least 25% less than the hydrolysis of the unmodified EET in a hydrolysis assay, more preferably 50% or more lower than the rate of hydrolysis of an unmodified EET. Liao and Zeldin show, for example, episulfide and sulfonamide EETs derivatives. Amide and ester derivatives of EETs and that are relatively stable are preferred embodiments. In preferred forms, the analogs or derivatives have the biological activity of the unmodified EET regioisomer from which it is modified or derived in reducing cardiac hypertrophy, dilated cardiomyopathy, or arrhythmia. Whether or not a particular EET analog or derivative has the biological activity of the unmodified EET can be readily determined by using it in the assays described in the Examples. As mentioned in the Definition section, above, for convenience of reference, the term "EETs" as used herein refers to unmodified EETs, and EETs analogs and derivatives unless otherwise required by context.

In some embodiments, the EET or EETs are embedded or otherwise placed in a material that releases the EET over time. Materials suitable for promoting the slow release of compositions such as EETs are known in the art. Optionally, one or more sEH inhibitors may also be placed in the slow release material.

Conveniently, the EET or EETs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". The choice of the particular enteric coating is not critical to the practice of the invention.

Assays for Epoxide Hydrolase Activity

Any of a number of standard assays for determining epoxide hydrolase activity can be used to determine inhibition of sEH. For example, suitable assays are described in Gill, et al., Anal Biochem 131, 273-282 (1983); and Borhan, et al., Analytical Biochemistry 231, 188-200 (1995)). Suitable in vitro assays are described in Zeldin et al., J. Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rilling, eds. 1985), Academic Press, Orlando, Fla., pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174:291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous method of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

Other Means of Inhibiting sEH Activity

Other means of inhibiting sEH activity or gene expression can also be used in the methods of the invention. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science. 305(5688):1289-92 (2004); He and Hannon, Nat Rev Genet. 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo. In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, "short interfering RNA" (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). The amino acid sequence of human sEH (SEQ ID NO:1) and the nucleotide sequence encoding that amino acid sequence (SEQ ID NO.:2) are set forth in U.S. Pat. No. 5,445,956.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and nonprofit researchers, from the Whitehead Institute for Biomedical Research on the internet by entering "http://" followed by "jura.wi.mit.edu/pubint/http://iona.wi.mit.edu/siRNAext/."

For example, using the program available from the Whitehead Institute, the following sEH target sequences and siRNA sequences can be generated:

```
                                              (SEQ ID NO: 3)
1) Target: CAGTGTTCATTGGCCATGACTGG (SEQ ID NO: 4)
Sense-siRNA: 5'-GUGUUCAUUGGCCAUGACUTT-3'

(SEQ ID NO: 5)
Antisense-siRNA: 5'-AGUCAUGGCCAAUGAACACTT-3'

(SEQ ID NO: 6)
2) Target: GAAAGGCTATGGAGAGTCATCTG (SEQ ID NO: 7)
Sense-siRNA: 5'-AAGGCUAUGGAGAGUCAUCTT-3'

(SEQ ID NO: 8)
Antisense-siRNA: 5'-GAUGACUCUCCAUAGCCUUTT-3'
```

-continued

```
                                              (SEQ ID NO: 9)
3) Target AAAGGCTATGGAGAGTCATCTGC (SEQ ID NO: 10)
Sense-siRNA: 5'-AGGCUAUGGAGAGUCAUCUUTT-3'

(SEQ ID NO: 11)
Antisense-siRNA: 5'-AGAUGACUCUCCAUAGCCUTT-3'

(SEQ ID NO: 12)
4) Target: CAAGCAGTGTTCATTGGCCATGA (SEQ ID NO: 13)
Sense-siRNA: 5'-AGCAGUGUUCAUUGGCCAUTT-3'

(SEQ ID NO: 14)
Antisense-siRNA: 5'-AUGGCCAAUGAACACUGCUTT-3'

(SEQ ID NO: 15)
5) Target: CAGCACATGGAGGACTGGATTCC (SEQ ID NO: 16)
Sense-siRNA: 5'-GCACAUGGAGGACUGGAUUTT-3'

(SEQ ID NO: 17)
Antisense-siRNA: 5'-AAUCCAGUCCUCCAUGUGCTT-3'
```

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase 111) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

```
                                              (SEQ ID NO: 19)
1) Target: CAGTGTTCATTGGCCATGACTGG (SEQ ID NO: 20)
Sense strand: 5'-GATCCCCGTGTTCATTGGCCATGACTTTCAA
GAGAAGTCATGGCCAATGAACACTTTTT-3'

(SEQ ID NO: 21)
Antisense strand: 5'-AGCTAAAAAGTGTTCATTGGCCATGACTT
CTCTTGAAAGTCATGGCCAATGAACACGGG-3'

(SEQ ID NO: 22)
2) Target: GAAAGGCTATGGAGAGTCATCTG (SEQ ID NO: 23)
Sense strand: 5'-GATCCCCAAGGCTATGGAGAGTCATCTTCAAGA
GAGATGACTCTCCATAGCCTTTTTTT-3'

(SEQ ID NO: 24)
Antisense strand: 5'-AGCTAAAAAAGGCTATGGAGAGTCATCT
CTCTTGAAGATGACTCTCCATAGCCTTGGG-3'

(SEQ ID NO: 25)
3) Target: AAAGGCTATGGAGAGTCATCTGC (SEQ ID NO: 26)
Sense strand: 5'-GATCCCCAGGCTATGGAGAGTCATCTTTCAAGA
GAAGATGACTCTCCATAGCCTTTTTT-3'

(SEQ ID NO: 27)
Antisense strand: 5'-AGCTAAAAAAGGCTATGGAGAG
TCATCATCTCTTGAAAGATGACTCTCCATAGCCTGGG-3'

(SEQ ID NO: 28)
4) Target: CAAGCAGTGTTCATTGGCCATGA (SEQ ID NO: 29)
Sense strand: 5'-GATCCCCAGCAGTGTTCATTGGCCATTTCAAGA
GAATGGCCAATGAACACTGCTTTTTT-3'

(SEQ ID NO: 30)
Antisense strand: 5'-AGCTAAAAAAGCAGTGTTCATTGGCCATT
CTCTTGAAATGGCCAATGAACACTGCTGGG-3'
```

-continued

5) Target: CAGCACATGGAGGACTGGATTCC (SEQ ID NO: 31)

Sense strand 5'-GATCCCCGCACATGGAGGACTGGATTTTCAAGAG AAATCCAGTCCTCCATGTGCTTTTT-3' (SEQ ID NO: 32)

Antisense strand: 5'-AGCTAAAAAGCACATGGAGGACTGGATTT CTCTTGAAAATCCAGTCCTCCATGTGCGGG-3' (SEQ ID NO: 33)

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264: 17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program on the internet which can be found by entering http://, followed by biotools.idtdna.com/antisense/AntiSense.aspx, which will provide appropriate antisense sequences for nucleic acid sequences up to 10,000 nucleotides in length. Using this program with the sEH gene provides the following exemplar sequences:

1) UGUCCAGUGCCCACAGUCCU     (SEQ ID NO: 34)

2) UUCCCACCUGACACGACUCU     (SEQ ID NO: 35)

3) GUUCAGCCUCAGCCACUCCU     (SEQ ID NO: 36)

4) AGUCCUCCCGCUUCACAGA      (SEQ ID NO: 37)

5) GCCCACUUCCAGUUCCUUUCC    (SEQ ID NO: 38)

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found by entering "www." followed by "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and 94/21797. Devices for accelerating particles into body tissues using compressed gases are described in, for example, U.S. Pat. Nos. 6,592,545, 6,475, 181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(11):4006-9 (2005); Brennecke et al., PLoS Biol. 3(3):e85 (2005). Methods of designing miRNAs are known. See, e.g., Zeng et al., Methods Enzymol. 392:371-80 (2005); Krol et al., J Biol. Chem. 279(40):42230-9 (2004); Ying and Lin, Biochem Biophys Res Commun. 326(3):515-20 (2005).

Therapeutic Administration

EETs and inhibitors of sEH can be prepared and administered in a wide variety of oral, parenteral and aerosol formulations. In preferred forms, compounds for use in the methods of the present invention can be administered by injection, that is, intravenously, intramuscularly, intracutaneously, subcutaneously, intraduodenally, or intraperitoneally. The sEH inhibitor or EETs, or both, can also be administered by inhalation, for example, intranasally. Additionally, the sEH inhibitors, or EETs, or both, can be administered transdermally. Accordingly, the methods of the invention permit administration of pharmaceutical compositions comprising a pharmaceutically acceptable carrier or excipient and either a selected inhibitor or a pharmaceutically acceptable salt of the inhibitor.

For preparing pharmaceutical compositions from sEH inhibitors, or EETs, or both, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

A therapeutically effective amount of the sEH inhibitor, or EETs, or both, is employed in inhibiting cardiac arrhythmia or inhibiting or reversing cardiac hypertrophy or dilated cardiomyopathy. The dosage of the specific compound for treatment depends on many factors that are well known to those skilled in the art. They include for example, the route of administration and the potency of the particular compound. An exemplary dose is from about 0.001 µM/kg to about 100 mg/kg body weight of the mammal.

EETs are unstable in acidic conditions, and can be converted to DHET. To avoid conversion of the EETs to DHET under the acidic conditions present in the stomach, EETs can be administered intravenously, by injection, or by aerosol. EETs intended for oral administration can be encapsulated in a coating that protects the EETs during passage through the stomach. For example, the EETs can be provided with a so-called "enteric" coating, such as those used for some brands of aspirin, or embedded in a formulation. Such enteric coatings and formulations are well known in the art. In some formulations, the EETs, or a combination of the EETs and an sEH inhibitor are embedded in a slow-release formulation to facilitate administration of the agents over time.

In another set of embodiments, an sEH inhibitor, one or more EETs, or both an sEH inhibitor and an EET are administered by delivery to the nose or to the lung. Intranasal and pulmonary delivery are considered to be ways drugs can be rapidly introduced into an organism. Devices for delivering drugs intranasally or to the lungs are well known in the art. The devices typically deliver either an aerosol of an therapeutically active agent in a solution, or a dry powder of the agent. To aid in providing reproducible dosages of the agent, dry powder formulations often include substantial amounts of excipients, such as polysaccharides, as bulking agents.

Detailed information about the delivery of therapeutically active agents in the form of aerosols or as powders is available in the art. For example, the Center for Drug Evaluation and Research ("CDER") of the U.S. Food and Drug Administration provides detailed guidance in a publication entitled: "Guidance for Industry: Nasal Spray and Inhalation Solution, Suspension, and Spray Drug Products—Chemistry, Manufacturing, and Controls Documentation" (Office of Training and Communications, Division of Drug Information, CDER, FDA, July 2002). This guidance is available in written form from CDER, or can be found on-line by entering "http://www." followed by "fda.gov/cder/guidance/4234fnl.htm". The FDA has also made detailed draft guidance available on dry powder inhalers and metered dose inhalers. See, Metered Dose Inhaler (MDI) and Dry Powder Inhaler (DPI) Drug Products—Chemistry, Manufacturing, and Controls Documentation, 63 Fed. Reg. 64270, (November 1998). A number of inhalers are commercially available, for example, to administer albuterol to asthma patients, and can be used instead in the methods of the present invention to administer the sEH inhibitor, EET, or a combination of the two agents to subjects in need thereof.

In some aspects of the invention, the sEH inhibitor, EET, or combination thereof, is dissolved or suspended in a suitable solvent, such as water, ethanol, or saline, and administered by nebulization. A nebulizer produces an aerosol of fine particles by breaking a fluid into fine droplets and dispersing them into a flowing stream of gas. Medical nebulizers are designed to convert water or aqueous solutions or colloidal suspensions to aerosols of fine, inhalable droplets that can enter the lungs of a patient during inhalation and deposit on the surface of the respiratory airways. Typical pneumatic (compressed gas) medical nebulizers develop approximately 15 to 30 microliters of aerosol per liter of gas in finely divided droplets with volume or mass median diameters in the respirable range of 2 to 4 micrometers. Predominantly, water or saline solutions are used with low solute concentrations, typically ranging from 1.0 to 5.0 mg/mL.

Nebulizers for delivering an aerosolized solution to the lungs are commercially available from a number of sources, including the AERx™ (Aradigm Corp., Hayward, Calif.) and the Acorn II® (Vital Signs Inc., Totowa, N.J.).

Metered dose inhalers are also known and available. Breath actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187, 748; 3,565,070; 3,814,297; 3,826,413; 4,592,348; 4,648,393; 4,803,978; and 4,896,832.

The formulations may also be delivered using a dry powder inhaler (DPI), i.e., an inhaler device that utilizes the patient's inhaled breath as a vehicle to transport the dry powder drug to the lungs. Such devices are described in, for example, U.S. Pat. Nos. 5,458,135; 5,740,794; and 5,785,049. When administered using a device of this type, the powder is contained in a receptacle having a puncturable lid or other access surface, preferably a blister package or cartridge, where the receptacle may contain a single dosage unit or multiple dosage units.

Other dry powder dispersion devices for pulmonary administration of dry powders include those described in Newell, European Patent No. EP 129985; in Hodson, European Patent No. EP 472598, in Cocozza, European Patent No. EP 467172, and in Lloyd, U.S. Pat. Nos. 5,522,385; 4,668, 281; 4,667,668; and 4,805,811. Dry powders may also be delivered using a pressurized, metered dose inhaler (MDI) containing a solution or suspension of drug in a pharmaceutically inert liquid propellant, e.g., a chlorofluorocarbon or fluorocarbon, as described in U.S. Pat. Nos. 5,320,094 and 5,672,581.

Without further elaboration, it is believed that one skilled in the art can, using the preceding description, practice the present invention to its fullest extent.

EXAMPLES

Example 1

This Example sets forth materials and methods used in studies underlying the present invention.

All animal care and procedures were approved by the University of California, Davis Institutional Animal Care and Use Committee and complied with the Guide for the Care and Use of Laboratory Animals (NIH publication No. 80-213, 1985).

Mouse Model of Pressure Overload

Ascending aortic constriction was performed in 8-week-old male C57B1/6J mice (Charles River, Wilmington, Mass.). Animals were anesthetized with intraperitoneal ketamine 50 mg/kg and xylazine 2.5 mg/kg, and aortic constriction was created via a left thoracotomy by placing a ligature securely around the ascending aorta and a 26-gauge needle and then removing the needle. Immediately after the surgery, animals with ascending aortic stenosis were randomized and placed in one of the following regimens for three weeks: (a) compound 950 in drinking water (100 mg/ml), (b) AUDA-BE in drinking water, or (c) no drug. Age-matched animals served as controls.

Analysis of Cardiac Function by Echocardiography

To assess systolic function, echocardiograms were performed using M-mode and two-dimensional measurements as described previously. The measurements represented the average of six selected cardiac cycles from at least two separate scans performed in random-blind fashion with papillary muscles used as a point of reference for consistency in level of scan. End diastole was defined as the maximal left ventricle diastolic dimension and end systole was defined as the peak of posterior wall motion. Fractional shortening (FS), a surrogate of systolic function, was calculated from left ventricle dimensions as follows: $FS=((EDD-ESD)/EDD)\times 100\%$.

Assessment of Left Ventricular Hypertrophy

To compare myocyte size, hearts were removed and rinsed for 1 minute in 0.1 mol/L phosphate buffered saline (PBS) with 50 mmol/L KCl (pH 7.2) and subsequently fixed overnight at 4° C. in 4% paraformaldehyde prepared in PBS. Vibratome sections (100 μm) from similar areas of the left ventricles were stained in a 1:20 dilution of rhodamine phalloidin (Molecular Probes, Inc., Eugene, Oreg.) and imaged with a BioRad MRC1000 confocal scanning laser microscope (BioRad Laboratories, Hercules, Calif.). A minimum of 5 optical sections was collected from the free wall of the left ventricle of each animal with a Zeiss 60× NA 1.4 lens. All images used for myocyte measurements were collected with identical laser, iris, gain, and black level operating parameters. Myocyte widths were measured parallel to the direction of the sarcomeres from unbranched regions of the myocytes near an intercalated disk with the length/profile function. Data sets were then compared using Student t tests.

In vivo Electrophysiologic Studies in Mice

In vivo electrophysiologic studies were performed as previously described. Standard pacing protocols were used to determine the electrophysiologic parameters, including sinus node recovery time, atrial, AV nodal, and ventricular refractory periods and AV nodal conduction properties. Each animal underwent an identical pacing and programmed stimulation protocol. The Q-T interval was determined manually by placing cursors on the beginning of the QRS and the end of the T wave. The rate-corrected QT interval (QTc) was calculated using modified Bazett's formula, whereby the RR interval was first expressed as a unitless ratio (RR in ms/100 ms). QTc interval was defined as QT interval (in ms)/(RR/100)1/2.

To induce atrial and ventricular tachycardia and fibrillation, programmed extrastimulation techniques and burst pacing were utilized. Programmed right atrial and right ventricular double and triple extrastimulation techniques were performed at 100-ms drive cycle length, down to a minimum coupling interval of 10 ms. Right atrial and right ventricular burst pacing were performed as eight 50-ms and four 30-ms cycle length trains episodes repeated several times, up to a maximum 1-min time limit of total stimulation. For comparison of the inducibility in each mouse, programmed extrastimulation techniques and stimulation duration of atrial and ventricular burst pacing were the same in all mice. Reproducibility was defined as greater than one episode of induced atrial or ventricular tachycardia.

Neonatal Mouse Cardiac Myocytes in Culture

Single cardiac myocytes were isolated from 5 day old neonatal mice (C57B1/6J) as previously described (Nuss & Marban, J. Physiol. 479 (Pt 2):265-79 (1994); Chiamvimonvat et al., J. Physiol. 483 (Pt 2):307-18 (1995)). Mice were anesthetized with pentobarbital (40 mg/kg) intraperitoneally. Animals were sacrificed by decapitation and hearts excised under sterile conditions into a filter sterilized (0.2 µm) nominally $Ca^{2+}$-, bicarbonate-free Hanks HEPES-buffered solution, pH 7.4 at room temperature. Atrial and great vessel tissues were carefully removed. The ventricles were washed and minced in this $Ca^{2+}$-free buffered solution containing trypsin (Difco®, BD Diagnostic Systems, Sparks Md., 1.5 mg/ml), DNase (1 ml/100 ml of the enzyme solution). The tissues were then incubated with 2 ml of the enzyme solution and stirred continuously at 37° C. The supernatant was removed and the enzyme solution replaced at five-minute intervals. The supernatant obtained after the first 15 minutes was discarded. Thereafter, the supernatant was diluted 1:1 in bovine calf serum. The cells were centrifuged at 2000 r.p.m. for three minutes and resuspended in MEM culture medium (Invitrogen, Carlsbad, Calif.) containing 5% bovine calf serum (Invitrogen), penicillin G (sodium) and vitamin B12. The viability of the cells was assessed using the trypan blue dye exclusion test. Generally, we obtained a viability of 90 to 98%. The cells were plated in tissue culture dishes and maintained at 37° C. in a 5% CO2 incubator and re-plated at a cell density of 1.5–2.5×105/ml after 20 minutes into new tissue culture dishes containing glass cover-slips (pre-treated with laminin in order to remove endothelial cells, which tend to attach to the tissue culture dishes during this 20-minute interval). Finally, cells were maintained at 37° C. in a 5% $CO_2$ incubator and were used for electrophysiological recording within 24-72 hours of cell isolation.

Statistical Analysis

Data were reported as means±SE. Student's t-test was used to test for differences between freshly isolated cell and cultured cell groups, and a paired t-test was used for assessing the significance of drug effects. A value of $P<0.05$ was considered to be statistically significant.

Example 2

This Example reports the results of studies in an animal model of cardiac hypertrophy.

Thoracic aortic constrictions ("TACs") were created in 8-week-old male C57B1/6J mice as described in Example 1, above, resulting in a chronic pressure overload induced cardiac hypertrophy. TAC-mice were randomized to receive either no therapy or one of two exemplar sEH inhibitors (compound 950 and AUDA-BE) in drinking water for a period of three weeks. An almost complete resolution of cardiac hypertrophy by the drug treatment was noted. This effect is independent of the anti-hypertensive action of the drugs, since the hearts were constantly exposed to the high afterload created by the aortic constriction.

FIG. 1 shows photomicrographs of examples of whole hearts from TAC-mice treated with compound 950 in the drinking water for three weeks compared to control untreated mice with TAC. All the mice were sacrificed at three weeks after the TAC was created. All the untreated TAC-mice showed the expected increased in heart size with dilatation of all chambers as previously described in this model. In contrast, the hearts of treated TAC-mice showed no evidence of cardiac hypertrophy.

Figure 2:
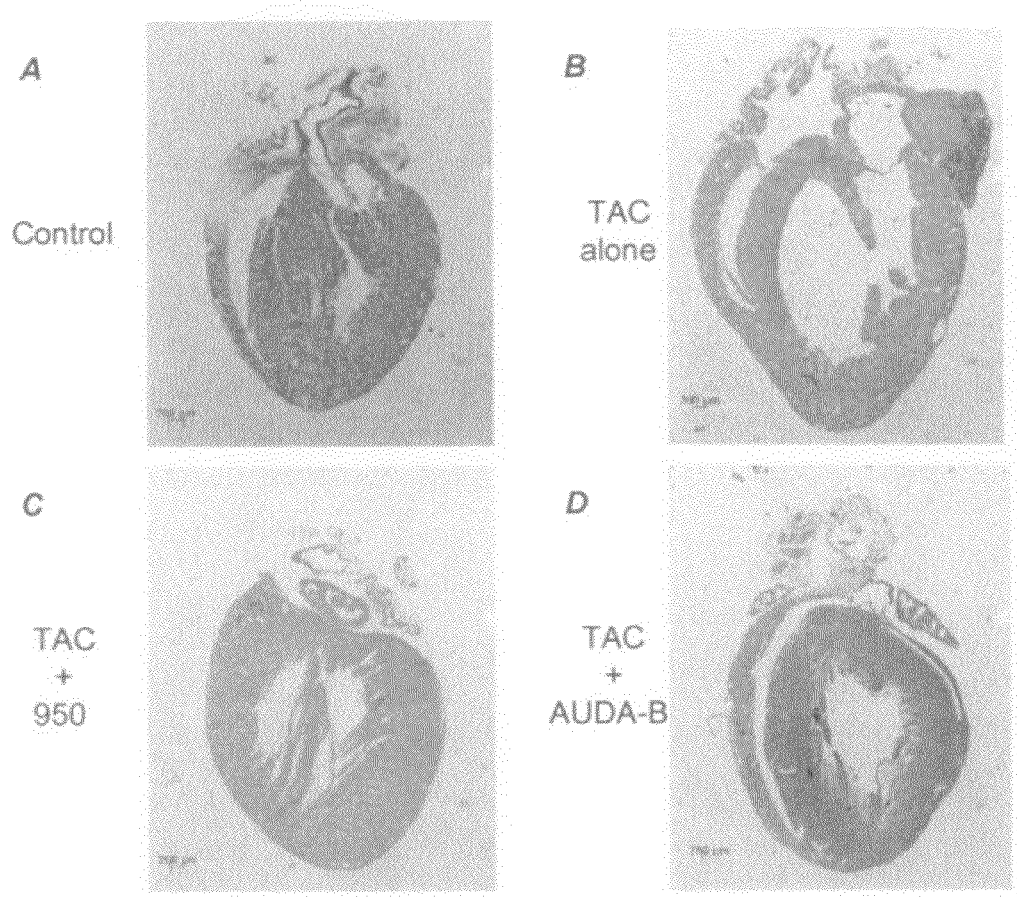
FIGS. 2A-D. Inhibition of cardiac hypertrophy in TAC-mice by sEH inhibitors compound 950 and AUDA-BE.
Figure 3:
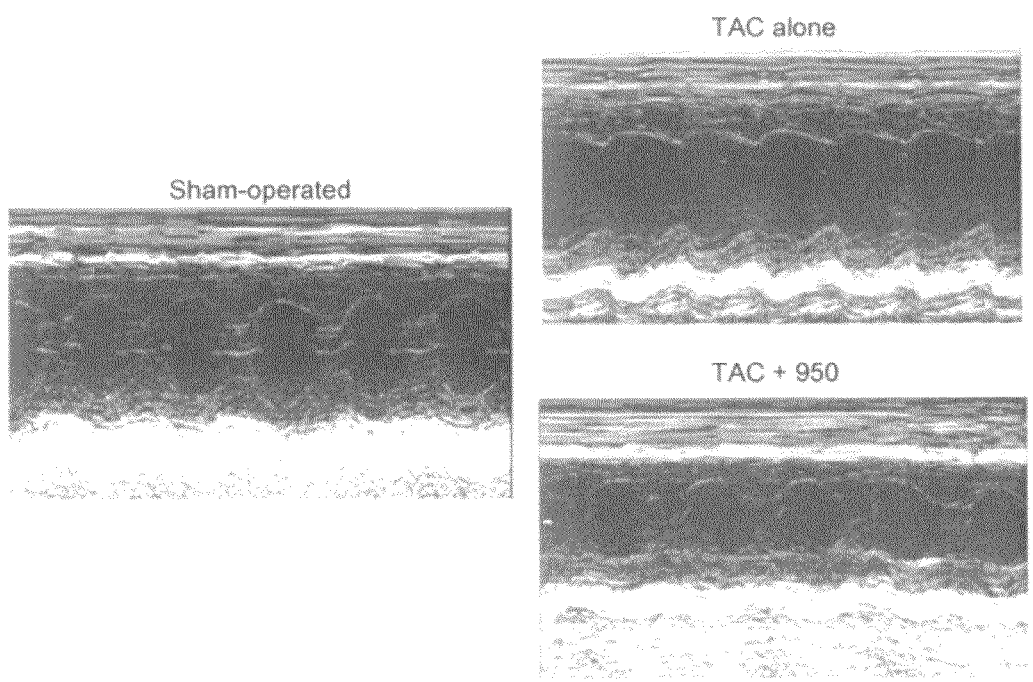
FIG. 3. M-mode echocardiography in sham-operated mice, TAC-mice, and TAC-mice treated with exemplar sEHI compound 950 after three weeks of treatment showing evidence of cardiac failure with chamber dilatation in TAC-mice. Compound 950 completely prevented the development of cardiac hypertrophy and failure in TAC-mice.
Figure 4:
FIG. 4. shows immunofluorescence confocal photomicrographs of sections of left ventricular myocytes stained with an anti-alpha actinin antibodies with secondary antibodies conjugated to Texas Red®. Sections were obtained from the left ventricles after three-week from sham-operated, TAC alone and TAC-mice treated with compound 950. The sham-operated mice showed ordered myofibrils. In contrast, hearts from TAC-mice shows loss of the organization of the myofibrils. The effects were prevented by the treatment with compound 950.

FIG. 2 further compares hematoxylin and eosin ("H&E")-stained histologic section of a sham-operated heart and of TAC-mouse hearts with or without sEHI treatment. The TAC-mouse showed evidence of cardiac hypertrophy and chamber dilatation. The hypertrophic response can be completely prevented using either compound 950 or AUDA-BE in the drinking water. We further assessed the chamber size and wall thickness in untreated TAC-mice compared to treated TAC-mice using echocardiography. As shown in FIG. 3, compound 950 can prevent the development of cardiac hypertrophy and failure in TAC mice after 3 and 6 weeks of follow up (see also Table 1). Furthermore, the myofibrils disarray which characterized the hypertrophic hearts were also prevented by treatment with sEH inhibitors (FIG. 4).

Figure 5:
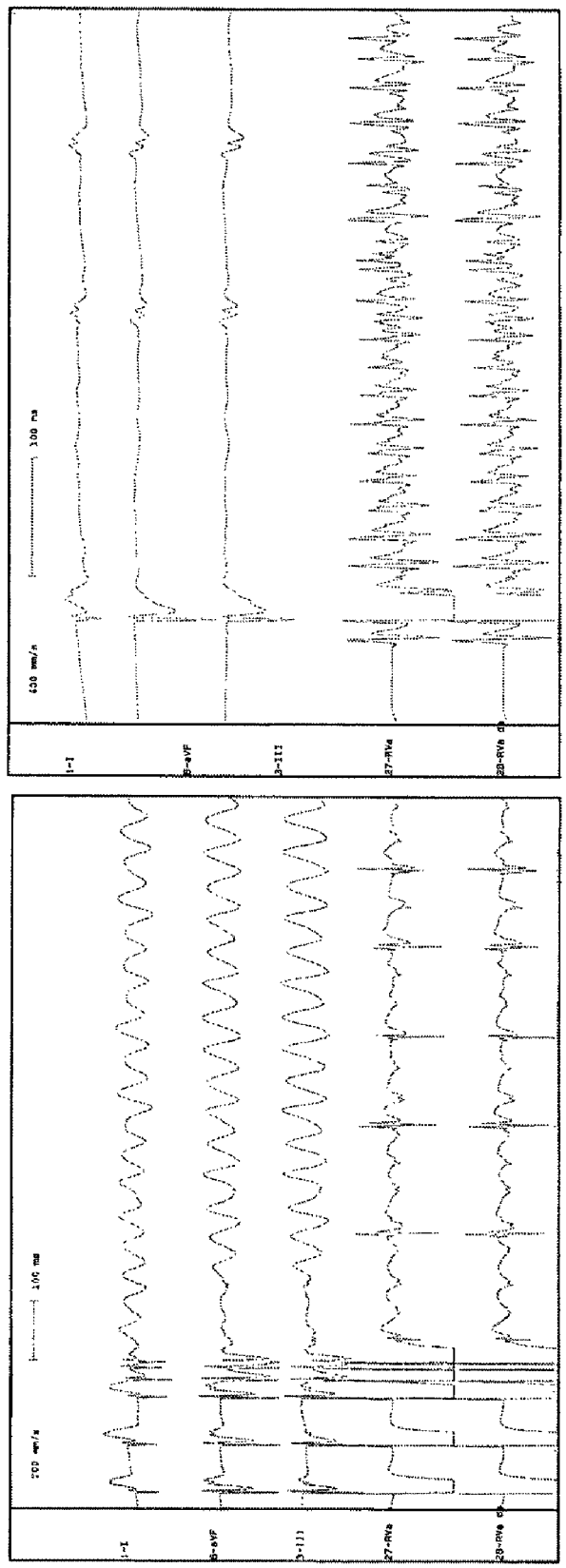
FIG. 5. In-vivo electrophysiologic study in untreated TAC-mice showing evidence of inducible ventricular tachycardia (left panel) and atrial fibrillation (right panel). Upper four tracing are surface ECG (Lead I, II, AVF and III). Lower two tracings are intracardiac electrogram showing atrial, and ventricular electrograms.
Figure 6:
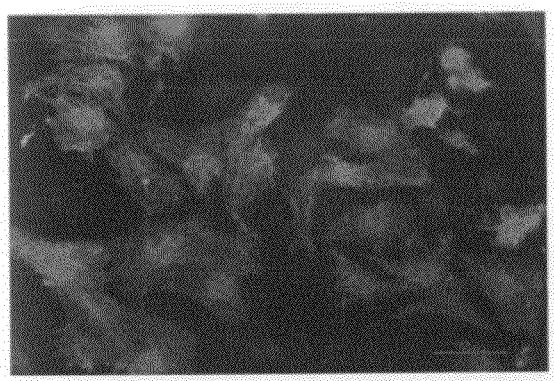
FIG. 6. Photomicrographs of primary neonatal mouse cardiac myocytes treated with angiotensin II (Ag II) to induce cardiac hypertrophy. Cells were then treated with anti-actinin antibodies and secondary antibody conjugated to Texas Red®. Upper panels show control neonatal cardiac myocytes and cells treated with Ag II alone (middle panel). Lower panel shows cells treated with Ag II and compound 950. Scale bars are 20 µm.
Figure 6:
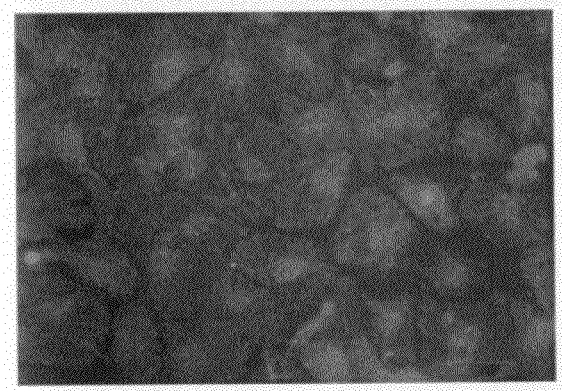
Figure 6:
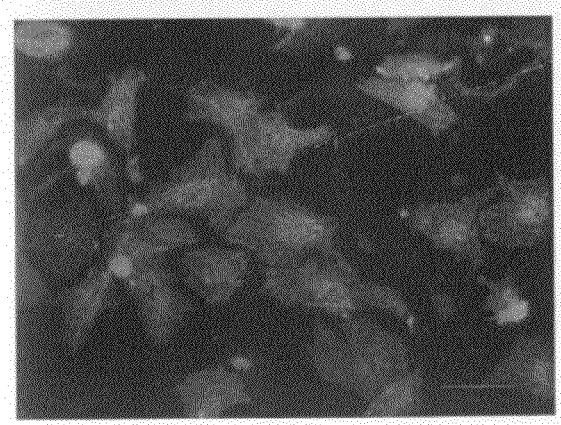

Example 3 sEH inhibitors have been previously investigated for the antihypertensive activities. Therefore, the question remained whether the antihypertrophic effects seen in Example 2 are the results of the antihypertensive activities of the sEHI. This was considered unlikely since our model produces a chronic constriction and a persistent increase in the afterload on the heart regardless of the systemic blood pressure. Nonetheless, to directly examine the effects of the sEH inhibitors on cardiac hypertrophy, a well documented model of in vitro neonatal cardiac myocytes and cardiac hypertrophy using phenylephrine or angiotensin II was adapted. Shown in the upper panels in FIG. 5 are confocal photomicrographs of primary culture of neonatal mouse cardiac myocytes treated with angiotensin II (ANG II) at low and higher magnification showing cells with cardiac hypertrophy after 48 hours of treatment with ANG II. Lower panels are of the same set of cells treated with both ANG II and with compound 950. There was a significant differences in the cell size in the neonatal cardiac myocytes of the cells treated with ANGII and with compound 950 compared to treatment with ANG II alone. These in vitro experiments further confirm our in vivo experiments that these compounds have a direct antihypertrophic effects independent of the antihypertensive activities of the drugs.

Example 4

It is well documented that there is significant electrical remodeling in cardiac hypertrophy and heart failure, leading to an increased in the susceptibility to cardiac arrhythmias. In order to further test whether sEH inhibitors have salutary effects on cardiac arrhythmias in the setting of cardiac hypertrophy, we performed in vivo electrophysiologic recordings in treated and untreated TAC-mice. In vivo electrophysiologic studies were conducted in mice using an in vivo Intracardiac Recording System (CardioLab, Prucka, GE Medical System). FIG. 4 shows examples of surface electrocardiogram and simultaneous intracardiac electrograms from atrium, ventricle as well as HIS bundle recording from treated and untreated TAC-mice using a CIB mouse EP catheter (2F, 18 mm, 8 electrodes, NuMED, Inc., Denton, Tex.). TAC-mice show evidence of both inducible atrial and ventricular arrhythmias with programmed stimulation. The susceptibility to increased cardiac arrhythmias was significantly suppressed using sEH inhibitors. Summary data is shown in Table 1.

TABLE 1

Incidence of inducible atrial and ventricular arrhythmias in untreated compared to treated TAC mice.

| Incidence | Atrial fibrillation | Ventricular fibrillation |
| --- | --- | --- |
| Sham operated | 0/9 (0%) | 0/9 (0%) |
| TAC alone | 3/9 (33%) | 6/9 (67%) |
| TAC + 950 | 0/6 (0%) | 1/6 (17%) |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting cardiomyopathy or cardiac arrhythmia in an subject in need thereof, said method comprising administering to said subject an effective amount of an inhibitor of soluble epoxide hydrolase ("sEH"), wherein the inhibitor of sEH has a urea, carbamate, or amide pharmacophore, wherein said subject does not have hypertension, or is not being treated for hypertension with an inhibitor of sEH, thereby inhibiting cardiomyopathy or cardiac arrhythmia in said subject.

2. A method of claim 1, wherein the cardiomyopathy is hypertrophic cardiomyopathy.

3. A method of claim 2, wherein said cardiac hypertrophy is due to valvular heart disease.

4. A method of claim 3, wherein said valvular heart disease is secondary to rheumatic fever, myxomatous degeneration of the valve, or papillary muscle dysfunction.

5. A method of claim 2, wherein said cardiac hypertrophy is due to myocardial infarction.

6. A method of claim 2, wherein said cardiac hypertrophy is due to familial hypertrophic cardiomyopathy.

7. A method of claim 1, wherein the cardiomyopathy is dilated cardiomyopathy.

8. A method of claim 7, wherein said dilated cardiomyopathy is alcohol induced cardiomyopathy.

9. A method of claim 7, wherein said dilated cardiomyopathy is familial dilated cardiomyopathy.

10. A method of claim 7, wherein said dilated cardiomyopathy is caused by administration of an anti-cancer drug or exposure to a toxic agent.

11. A method of claim 1, wherein the administration of said agent or agents inhibits cardiac arrhythmia.

12. A method of claim 11, wherein the arrhythmia is atrial fibrillation.

13. A method of claim 11, wherein the arrhythmia is ventricular fibrillation.

14. A method of claim 11, wherein the arrhythmia is ventricular tachycardia.

15. A method of claim 1, wherein said inhibitor of sEH is an adamantyl dodecyl urea.

16. A method of claim 1, wherein said inhibitor of sEH is selected from the group consisting of 12-(3-Adamantan-1-yl-ureido)dodecanoic acid, 12-(3-Adamantan-1-yl-ureido) dodecanoic acid butyl ester, Adamantan-1-yl-3-{5-[2-(2-ethoxyethoxy)ethoxy]pentyl}urea, and N-(1-acetylpiperidin-4-yl)-N'-(adamant-1-yl)urea.

17. A method of claim 1, wherein the inhibitor of sEH is in a material which releases the inhibitor of sEH over time.

18. A method of claim 1, in which the wherein the inhibitor of sEH is released from a stent placed in a coronary artery.

19. A method of claim 1, wherein the inhibitor of sEH has an $IC_{50}$ of less than about 500 μM.

20. A method of claim 1, wherein the cardiomyopathy is arrhythmogenic right ventricular cardiomyopathy (ARVC).

21. A method of claim 1, wherein the subject has overt heart failure.

22. A method of claim 1, wherein the subject has cardiac fibrous scarring and/or fibrosis.

* * * * *